United States Patent [19]

Carignan et al.

[11] Patent Number: 4,955,916

[45] Date of Patent: Sep. 11, 1990

[54] THUMB JOINT PROSTHESIS

[75] Inventors: Roger G. Carignan, Thousand Oaks, Calif.; Stanley H. Nahigian, Hunting Valley, Ohio; Clyde R. Pratt, Somis, Calif.

[73] Assignee: Techmedica, Inc., Camarillo, Calif.

[21] Appl. No.: 345,298

[22] Filed: May 1, 1989

[51] Int. Cl.[5] .......... A61F 2/42

[52] U.S. Cl. .......... 623/21; 623/23

[58] Field of Search .......... 623/21, 23

[56] References Cited

U.S. PATENT DOCUMENTS

| | | | |
|---|---|---|---|
| 3,894,297 | 7/1975 | Mittelmeier et al. | 623/23 |
| 4,276,660 | 7/1981 | Laure | 623/21 |
| 4,304,011 | 12/1981 | Whelan, III | 623/21 |
| 4,313,232 | 2/1982 | Habal et al. | 623/21 |
| 4,352,212 | 10/1982 | Greene et al. | 623/21 |
| 4,642,122 | 2/1987 | Steffee | 623/21 |

FOREIGN PATENT DOCUMENTS

| | | | |
|---|---|---|---|
| 0201407 | 11/1986 | European Pat. Off. | 623/23 |

*Primary Examiner*—Randall L. Green
*Assistant Examiner*—Stephanie L. Iantorno
*Attorney, Agent, or Firm*—Cislo & Thomas

[57] ABSTRACT

An improved carpal-metacarpal thumb joint prosthesis comprising carpal and metacarpal components which are tapered and threaded to facilitate fixation and to promote bone ingrowth together with a recess formed in the carpal component for holding a mesh disc to further enhance bone in-growth and having the carpal component formed generally U-shaped cavity containing an insert formed of ultrahigh molecular weight polyethylene which receives the spherical end of a tapered head which is securely received in a corresponding cavity within the metacarpal component.

7 Claims, 1 Drawing Sheet

THUMB JOINT PROSTHESIS

BACKGROUND OF THE INVENTION

This invention relates to prosthetic devices for surgical implantation in a human body and is particularly directed to a thumb joint prosthesis for replacement of the carpal-metacarpal thumb joint.

Prosthetic devices for replacement of many parts of the human body have been developed in recent years. The development of any prosthetic device presents numerous problems and it will be apparent that prosthetic devices for replacing joints present unique difficulty since joints must be capable of movement and, preferably, should simulate as closely as possible the movement of the joint which the device is designed to replace.

While most human joints flex in only one plane, a few joints, such as the hip, shoulder and the carpal-metacarpal thumb joint are movable throughout substantially an entire hemisphere. Obviously, creating prostheses for these joints is especially difficult.

Several attempts have been made to provide carpal-metacarpal thumb joint prosthesis. However, none of the prior art devices have been entirely satisfactory. Some of the prior art devices have been extremely complex and, hence, would be very expensive to produce and may be highly subject to failure. Other prior art devices have been unduly bulky and, thus, would be difficult or impossible to implant. Still other prior art devices have provided only very limited movement and, consequently, do not provide adequate replacements for the original joint. A number of relevant patents have been found in the U.S. Patent Office and are listed below:

| U.S. PAT. NO. | INVENTOR | ISSUE DATE |
|---|---|---|
| 2,422,302 | B. Horn | Jun. 17, 1947 |
| 3,694,821 | W. D. Mortiz | Oct. 3, 1972 |
| 4,059,854 | G. R. Laure | Nov. 29, 1977 |
| 4,106,128 | A. S. Greenwald et al | Aug. 15, 1978 |
| 4,180,871 | R. S. Hamas | Jan. 1, 1980 |
| 4,213,208 | S. Marne | Jul. 22, 1980 |
| 4,321,121 | F. M. Lewis | Nov. 4, 1980 |
| 4,259,752 | J. Taleisnik | Apr. 7, 1981 |
| 4,276,660 | G. R. Laure | Jul. 7, 1981 |
| 4,304,011 | E. J. Whelan III | Dec. 8, 1981 |
| 4,352,212 | D. J. Greene et al | Oct. 5, 1982 |
| 4,636,218 | I. Fukuura et al | Jan. 13, 1988 |

Described below are some of the more pertinent patents. Reference numbers used below pertain to the disclosures of the described patents.

The patent to Greene et al, Pat. No. 4,352,212, discloses a carpal-phalangeal joint prosthesis consisting of a plastic metacarpal intramedullary plug 3, a metacarpal component 5 consisting of a housing member 6, a plastic bearing insert 7, a metal phalangeal component 9 and a plastic phalangeal intramedullary plug 11. However, the phalangeal component 9 can only rotate in two planes due to its geometry.

The patent to Whelan III, Pat. No. 4,304,011, discloses a phalangeal joint prosthesis having a proximal component 12 consisting of a proximal capsule 22 formed from silicon rubber and a proximal core member 24 formed of stainless alloy with the core being substantially enclosed in the proximal capsule 22. The proximal component 12 additionally includes a bearing cup 28 formed of polyethylene and received in a cup-like socket 31. The cup-like socket 31 is unitarily attached to the large end of the tapered stem 32 of the proximal metal core member 24. However, the outer surface of the polyethylene bearing cup 28 is provided with a protruding retaining flange 34 which is matedly received in a groove 36 in the interior of the surface of the cup socket 31.

The patent to Greenwald et al, Pat. No. 4,106,128, discloses a radial component 10, a concavo-convex socket component 20 and a metacarpal component 30. The radial component 10 comprises a radial intramedullary stem 11 integral with a radial cup 13. The interior surface 14 of the cup 13 is generally concave. The concavo-convex component 20 has a convex surface 21 which mates with the concave surface 14 of cup 13. The socket is made of a compatible plastic, such as a high density polyethylene.

The patent to Fukuura et al, Pat. No. 4,636,218, is directed to a ball-and-socket prosthetic joint, but is intended as a hip replacement and shows that each of the members is threadedly coupled to the bone tissue. However, these threads or grooves are used to enhance adhesive bodies and are not used as the method of fixation in themselves. Also, the Fukuura device has no polyethylene insert.

The remaining patents listed are of general interest only. Thus, those prior art prosthesis are not any more relevant to the present invention.

SUMMARY OF THE INVENTION

The prosthetic device of the present invention comprises carpal and metacarpal components which are tapered and threaded to facilitate fixation and to promote bone in-growth together with a recess formed in the carpal component for holding a mesh disc to further enhance bone in-growth and having the carpal component forming generally a U-shaped cavity containing an insert formed of ultrahigh molecular weight polyethylene which receives the spherical end of a tapered head which is shrink-fit into a corresponding cavity within the metacarpal component.

Accordingly, it is an object of the present invention to provide an improved carpal-metacarpal thumb joint prosthesis.

A further object of the present invention is to provide an improved carpal-metacarpal thumb joint prosthesis having tapered and threaded carpal and metacarpal components to facilitate fixation and to promote bon in-growth.

Another object of the present invention is to provide an improved carpal-metacarpal thumb joint prosthesis having a carpal component formed with a generally U-shaped recess containing an insert formed of ultrahigh molecular weight polyethylene configured to receive the spherical end of a tapered head which is secured to the metacarpal component to provide freedom of movement.

A specific object of the present invention is to provide an improved carpal-metacarpal thumb joint prosthesis comprising carpal and metacarpal components which are tapered and threaded to facilitate fixation and to promote bone in-growth together with a recess formed in the carpal component for holding a mesh disc to further enhance bone in-growth and having the carpal component forming a generally U-shaped cavity containing an insert formed of ultrahigh molecular weight polyethylene which receives the spherical end of a tapered head which is shrink-fit into a corresponding cavity within the metacarpal component.

These and other objects and features of the present invention will be apparent from the following detailed description taken with reference to the figures of the accompanying drawing.

DESCRIPTION OF THE PREFERRED EMBODIMENT

Figure 1:
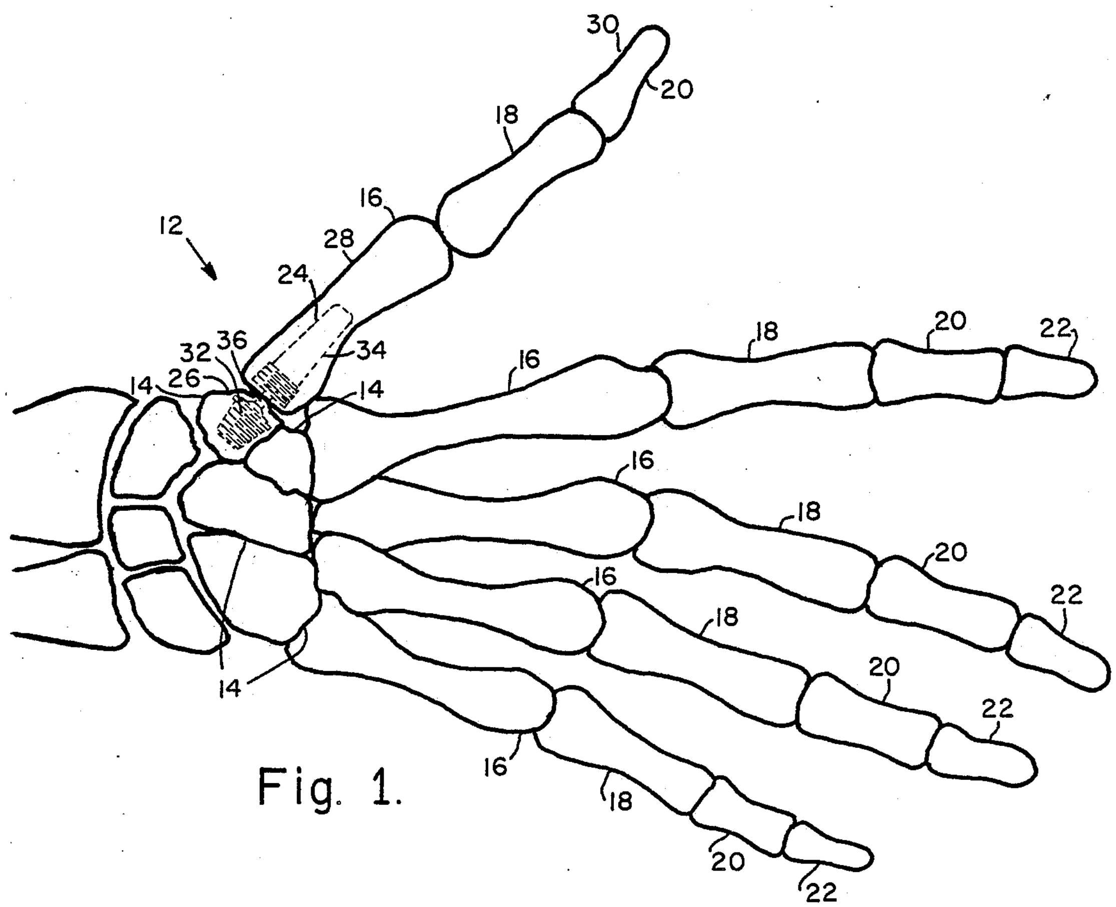
FIG. 1 is a diagrammatic representation showing the thumb joint prosthesis of the present invention implanted in a human hand.

In that form of the present invention chosen for purposes of illustration in the drawing, FIG. shows a diagram of the bones of a human hand, indicated generally at 12. The bones of the hand 12 comprise carpal bones 14, metacarpal bones 16, first phalanges 18, second phalanges 20 and third phalanges 22. As shown, the thumb prosthesis of the present invention, indicated generally at 24, is implanted between the carpal bone 26 and the metacarpal bone 28 of the thumb 30.

The prosthesis 24 comprises a carpal component 32, which is implanted in the carpal bone 26 of the thumb 30, and a metacarpal component 34, which is implanted in the metacarpal bone 28 of the thumb 30. An intermediate member 36 serves to connect the carpal component 32 and the metacarpal component 34.

Figure 2:
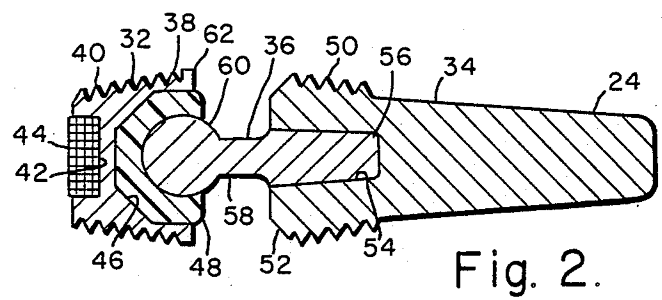
FIG. 2 is a vertical section through the thumb joint prosthesis of FIG. 1.
Figure 3:
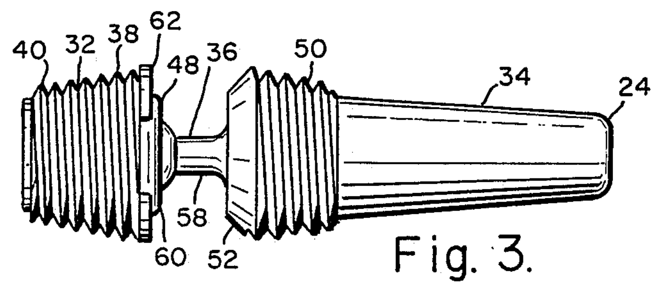
FIG. 3 is a side view of the thumb joint prosthesis of FIG. 1.

As best seen in FIGS. 2 and 3, the carpal component 32 of the prosthesis 24 is a concave member having a rearwardly tapered exterior 38 formed with external threads 40 and having a recess 42 formed in the rear end of the carpal component 32 to receive a mesh disk 44, the mesh preferably being of titanium.

Internally, the carpal component 32 is formed with a recess 46 in which is mounted an insert 48 formed of ultrahigh molecular weight polyethylene. The metacarpal component 34 is an elongated tapered member having an externally threaded portion 50 located adjacent its rear end 52.

The metacarpal component 34 is also formed with a forwardly tapered recess 54 extending axially forward from the rear end 52. The intermediate member 36 has a tapered forward end portion 56 which is shrink fit into the recess 54 of the metacarpal component 34 and has a neck portion 58 which extends rearwardly from the tapered forward end portion 56 and terminates in a spherical portion 60 which is rotatably retained within the polyethylene insert 48 of the carpal component 32 to connect the carpal component 32 to the metacarpal component 34.

To implant the prosthesis 24, a hole, having a diameter slightly smaller than the forward end 62 of the carpal component 32, is drilled into the carpal bone 26 of the thumb 30 and the carpal component 32 is threaded into this hole. Since the forward end 62 of the carpal component 32 has a slightly greater diameter than the hole, some stress is applied to the carpal bone which, together with the mesh disk 44 in recess 42 of the carpal component 32 serves to enhance bone in-growth and permanent fixation of the carpal component.

Similarly, a hole having a diameter slightly smaller than that of rear end 52 of the metacarpal component 34 is drilled into the metacarpal bone 28 of the thumb 30 and the metacarpal component 34 is threaded into that hole. Again, the fact that the diameter of end 52 of the metacarpal component 34 is slightly greater than the diameter of the hole causes some stress on the metacarpal bone 28 which enhances bone in-growth and permanent fixation of the metacarpal component 34.

The intermediate member 36 is initially independent from the metacarpal component 34, subsequently its spherical end 60 is rotatably mounted in the polyethylene insert 48 of the carpal component 32. When the carpal component 32 is implanted, the intermediate member 36 is already attached to the carpal component 32. Then, the metacarpal component 34 is implanted and, thereafter, tapered end 56 of the intermediate member 36 is inserted into the recess 54 of the metacarpal component 34.

Because the tapered end 56 of the intermediate member 36 is securely received in the recess 54 of the metacarpal component 34, the tapered end 56 forms a strong frictional bond with the metacarpal component once the tapered end 56 is inserted into the recess 54. Thus, the carpal component 32 and the metacarpal component 34 of the prosthesis 24 are fixedly implanted in the bones 26 and 28 of the thumb 30 and are strongly connected by the taper fit of the tapered end 56 of the intermediate member 36 within the recess 54 of the metacarpal member, while the spherical end 60 of the intermediate member 36 is rotatably shrink fit mounted within the polyethylene insert 48 of the carpal component and, hence, permits free rotation of the metacarpal component 34 and the metacarpal bone 28 of the thumb 30 throughout substantially an entire hemisphere.

Obviously, numerous variations and modifications can be made to the prosthesis of the present invention without departing from the spirit of the invention. Therefore, it should be clearly understood that the form of the present invention described above and shown in the accompanying drawings is illustrative only and is not intended to limit the scope of the present invention.

We claim:

1. An improved carpal-metacarpal thumb joint prosthesis comprising:

a carpal component having a forward end and a rear end and having a tapered and threaded exterior and a generally U-shaped interior cavity;

a metacarpal component having a forward end and a rear end and having a tapered and threaded exterior and an axial recess extending inwardly from the rear end thereof an insert formed of ultrahigh molecular weight polyethylene mounted in said cavity of said carpal component, said insert having a recess with curved interior walls; and an intermediate member having a tapered forward end adapted to securely mate within said recess in said metacarpal component, a spherical rear end rotatably and captively mounted within said recess in said polyethylene insert in said carpal component and a neck portion connecting said forward end of said intermediate member to said rear end of said intermediate member.

2. The prosthesis of claim 1, wherein:

the exterior of said carpal component is tapered rearwardly.

3. The prosthesis of claim 1, wherein:

the exterior of said metacarpal component is tapered forwardly.

4. The prosthesis of claim 1 further comprising:

a carpal component having a recess formed in an exterior surface thereof and a mesh disk captively secured within said recess.

5. The prosthesis of claim 1, wherein:

said metacarpal component is elongated and has a taper extending away from said intermediate member.

6. A prosthesis for carpal-metacarpal joining in the human hand allowing a carpal bone to be joined with a metacarpal bone and allowing a range of motion similar to the original joint, comprising:

a metacarpal component of a surgically implantable material which is forwardly tapered having a forward and narrower end which may be implanted into a hole formed within the metacarpal bone to be joined, and wherein said metacarpal component has a rearward and wider end having threading to engage the metacarpal bone upon implantation, and wherein said wider end defines an axially located bore of a predetermined diameter which forwardly tapers, and a carpal component of a surgically implantable material having a rearward end, tapering narrowly for implantation into a hole formed within the carpal bone to be joined, and a wider having threading to engage the carpal bone upon implantation, and wherein said forward end of said carpal component defines a first recess of a concave geometry, centered axially to said carpal component, and wherein said carpal component has a second concave recess in the rear end surface thereof and being centered axially to said carpal component, and a mesh disk to promote bone ingrowth is fitted within said second recess of said carpal component, allowing the carpal bone to join to said carpal component after implantation of the prosthesis, and an ultrahigh molecular weight polyethylene insert which can be fitted into said first recess of said carpal component for secure attachment to said carpal component, wherein said insert defines a third concave recess located axially to said insert of a size smaller than said first recess, and an intermediate component having a spherical ball, and an elongated tapering end interconnected through a neck portion, said intermediate component joining said carpal component to said metacarpal component and allowing hemispherical rotation of each component with respect to the other, wherein said spherical ball is captively held within said third recess of said insert, and wherein said elongated end is of a size and shape to be matingly received within said bore of said metacarpal component.

7. An improved carpal-metacarpal thumb join prosthesis comprising:

a carpal component having a forward end and a rear end and having a tapered and threaded exterior and a generally U-shaped interior cavity and a recess formed in said rear end of said carpal component, and a mesh disk operatively mounted in said recess to enhance bone ingrowth a metacarpal component having a forward end and a rear end and having a tapered and threaded exterior and an axial recess extending inwardly from said rear end thereof;

an insert formed of ultrahigh molecular weight polyethylene mounted in said cavity of said carpal component, and an intermediate member having a tapered forward end adapted to securely mate within said recess in said metacarpal component, a spherical rear end rototably mounted in said polyethylene insert in said carpal component and a neck portion connecting said forward end to said rear end.

* * * * *